United States Patent
Mestha et al.

(10) Patent No.: US 6,975,949 B2
(45) Date of Patent: Dec. 13, 2005

(54) FULL WIDTH ARRAY SCANNING SPECTROPHOTOMETER

(75) Inventors: Lalit K. Mestha, Fairport, NY (US); Jagdish C. Tandon, Fairport, NY (US); Steven B. Bolte, Rochester, NY (US)

(73) Assignee: Xerox Corporation, Stamford, CT (US)

( * ) Notice: Subject to any disclaimer, the term of this patent is extended or adjusted under 35 U.S.C. 154(b) by 37 days.

(21) Appl. No.: 10/833,231

(22) Filed: Apr. 27, 2004

(65) Prior Publication Data

US 2005/0240366 A1   Oct. 27, 2005

(51) Int. Cl.$^7$ .................. G01R 23/16; G01N 21/25; G03B 27/00; G01J 3/51
(52) U.S. Cl. .................. 702/76; 355/1; 356/402; 356/419
(58) Field of Search .................. 702/27, 75, 76, 702/196; 250/216, 566; 347/238, 244, 251; 355/1; 356/319, 320, 402, 406, 419, 420; 358/1.9, 504

(56) References Cited

U.S. PATENT DOCUMENTS

| | | | |
|---|---|---|---|
| 4,982,222 A | * | 1/1991 | Rees .................. 355/1 |
| 5,481,380 A | | 1/1996 | Bestmann .................. 358/504 |
| 5,963,244 A | | 10/1999 | Mestha et al. .................. 347/251 |
| 6,031,618 A | | 2/2000 | Wang .................. 356/419 |
| 6,178,007 B1 | | 1/2001 | Harrington .................. 358/1.9 |
| 6,320,182 B1 | | 11/2001 | Hubble, III et al. .................. 250/216 |
| 6,351,308 B1 | | 2/2002 | Mestha .................. 356/402 |
| 6,384,918 B1 | | 5/2002 | Hubble, III et al. .................. 356/402 |
| 6,449,045 B1 | | 9/2002 | Mestha .................. 356/402 |
| 6,538,770 B1 | | 3/2003 | Mestha .................. 358/1.9 |
| 6,556,300 B2 | | 4/2003 | Tandon et al. .................. 356/419 |
| 6,556,932 B1 | | 4/2003 | Mestha et al. .................. 702/76 |
| 6,567,170 B2 | | 5/2003 | Tandon et al. .................. 356/406 |
| 6,584,435 B2 | | 6/2003 | Mestha et al. .................. 702/196 |
| 6,587,793 B2 | | 7/2003 | Viassolo et al. .................. 702/27 |
| 6,621,576 B2 | | 9/2003 | Tandon et al. .................. 356/320 |
| 6,639,669 B2 | | 10/2003 | Hubble, III et al. .................. 356/319 |
| 6,663,382 B2 | | 12/2003 | Li .................. 431/153 |
| 6,690,471 B2 | | 2/2004 | Tandon et al. .................. 356/420 |

OTHER PUBLICATIONS

U.S. Appl. No. 10/758,096, filed Jan. 16, 2004, Mestha, et al, "Reference Database and Method for Obtaining Spectra Using Measurements From an LED Color Sensor and Method of Generating a Reference Database".

U.S. Appl. No. 10/093,220, filed Mar. 6, 2003, Balasubramanian, et al, "Use of Spectral Sensors for Automatic Media Identification and Improbed Scanner Correction".

\* cited by examiner

Primary Examiner—Michael Nghiem
Assistant Examiner—John Le

(57) ABSTRACT

A full width array spectrophotometer for full width scanning color analysis of color test targets, with one or two substantially linear elongated arrays of closely spaced multiple LED illumination sources of plural different color emissions in a multiply repeated pattern of at least three or four different colors transversely spanning a printer paper path and sequentially illuminated to illuminate a transverse band across a printed sheet moving in the paper path, and a corresponding elongated low cost light imaging bar with a parallel and correspondingly elongated array of multiple closely spaced different color sensitive (three or four rows of color-filtered) photodetectors, which imaging bar is positioned to detect and analyze light reflected from the transverse sequentially illuminated band.

10 Claims, 3 Drawing Sheets

FULL WIDTH ARRAY SCANNING SPECTROPHOTOMETER

Reference is made to commonly assigned applications, U.S. Application Ser. No. 09/941,858, filed Aug. 30, 2001, by Lingappa K. Mestha, et al, entitled "Systems and Methods for Determining Spectra Using Dynamic Least Squares Algorithms with Measurements from LED Color Sensor" published on Mar. 20, 2003 as U.S. Publication No. 2003/0055611, now U.S. Pat. No. 6,721,692 issued Apr. 13, 2004; and U.S. Application Ser. No. 10/758,096, filed Jan. 16, 2004, by the same L. K. Mestha, et al, entitled "Reference Database and Method for Obtaining Spectra Using Measurements From an LED Color Sensor and Method of Generating a Reference Database" published on Jul. 21, 2005 as U.S. Publication No. 2005/0160092.

Disclosed in the embodiments herein is a full width array color spectrophotometer scanning system particularly suitable for high speed on line document color analysis (including grey scale analysis), with at least one full width array plural colors illumination system and a full width array plural colors photodetector system using a low cost full width array imager bar.

Various types of color spectrophotometer systems are known in the art, including on-line systems for measurement and control of the printed output of color printers. The following published or issued Xerox Corp. patent disclosures are noted by way of some examples: U.S. Pat. No. 6,384,918 B1, issued May 7, 2002 to Fred F. Hubble, III, et al, entitled "Spectrophotometer For Color Printer Control With Displacement Insensitive Optics"; U.S. Pat. No. 6,663,382 B2, issued Oct. 14, 2003 to Fred F. Hubble, III, et al, entitled "Angular, Azimuthal and Displacement Insensitive Spectrophotometer For Color Printer Color Control Systems"; U.S. Pat. No. 6,639,669 B2, issued Oct. 28, 2003 to Fred F. Hubble, III, et al, entitled "Diagnostics for Color Printer On-Line Spectrophotometer Control System"; U.S. Pat. No. 6,351,308, issued Feb. 26, 2002 to Lingappa K. Mestha, entitled "Color Printer Color Control System with Automatic Spectophotometer Calibration System"; and U.S. Pat. No. 6,538,770, issued Mar. 25, 2003 to Lingappa K. Mestha, entitled "Color Printer Color Control System Using Dual Mode Banner Color Test Sheets". Also the above-cited U.S. application Ser. No. 10/758,096, filed Jan. 16, 2004, by the same L. K. Mestha, et al, entitled "Reference Database and Method for Obtaining Spectra Using Measurements From an LED Color Sensor and Method of Generating a Reference Database" published on Jul. 21, 2005 as U.S. Publication No. 2005/0160092.

Particularly noted are Xerox Corp. U.S. Pat. No. 6,690,471 B2, issued Feb. 10, 2004 to Jagdish C. Tandon and Lingappa K. Mestha, entitled "Color Imager Bar based Spectrophotometer For Color Printer Color Control System"; and Xerox Corp. U.S. Pat. No. 6,621,576 B2, issued Sep. 16, 2003 to Jagdish C. Tandon and Lingappa K. Mestha, entitled "Color Imager Bar based Spectrophotometer For Color Printer Color Control System".

Additional noted background references are: U.S. Pat. No. 6,567,170, issued May 20, 2003 to Jagdish C. Tandon et al, entitled "Simultaneous Plural Colors Analysis Spectrophotometer"; U.S. Pat. No. 6,449,045, issued Sep. 10, 2002 to Lingappa K. Mestha, entitled "System and Method for Reconstruction of Spectral Curves, Using Measurements from a Color Sensor and Statistical Techniques"; U.S. Pat. No. 6,556,932, issued Apr. 29, 2003 to Lingappa K. Mestha, et al, entitled "System and Method for Reconstruction of Spectral Curves Using Measurements from a Color Sensor and a Spectral Measurement System Model"; U.S. Pat. No. 6,584,435, issued Jun. 24, 2003 to Lingappa K. Mestha, et al, entitled "Systems And Methods For Determining Spectra Using Dynamic Karhunen-Loeve Algorithms With Measurements From Led Color Sensor"; U.S. Pat. No. 6,587,793, issued Jul. 1, 2003 to Daniel E. Viassolo, et al, entitled "Systems and Methods for Determining Spectra Using Fuzzy Inference Algorithms with Measurements from LED Color Sensor"; and U.S. Pat. No. 6,320,182, issued Nov. 20, 2001 to Fred F. Hubble, III, et al, entitled "Light Collector for an LED Array". Also, Xerox Corp. Steven J. Harrington U.S. Pat. No. 6,178,007 B1.

Further by way of background, current document scanners typically sense colors in terms of RGB coordinates, which approximate the human visual system. Usually, scanner characterization is needed to transform scanned RGB values (scanner output signals) to colorimetric (i.e. visual) signals. Most scanners are deviant from the human visual system in ways that differ depending on the media and inks being scanned. To address this problem, different characterizations or profiles or corrections to profiles may be built for different media or ink. This is typically accomplished by scanning test patches on test sheets with known colorimetric values, extracting the scanner RGB signals for each of the patches, and building a profile that maps scanner RGB to a calorimetric space. This process is then repeated for multiple different test media sheets. That printed output color information can then be used to control various printing or printer parameters. Note the descriptions in the above patents and applications and other art cited therein, and Xerox Corp. U.S. Pat. No. 5,963,244 issued Oct. 5, 1999 to L. K. Mestha, et al, and entitled "Optimal Reconstruction of Tone Reproduction Curve."

There are at least two problems with said current scanner characterization solutions: (1) the user may have to select the correct profile for processing a given scan depending on the particular print medium and the particular inks (herein broadly encompassing liquid or solid inks or toners), (2) even when the correct profile is chosen, there can be sufficient variation in input materials even within a given print media class to give rise to objectionable errors in scanner color correction system. In a recent study, more than 50% of users asked to identify the media by examining prints from photographic, offset, and inkjet printers were not able to do so correctly. The error that arises from choosing the incorrect scanner profile can be considerable. If a scanner is corrected for a photographic medium, and the test scan is also from the same medium, it was found that the average scanner correction error for a test set of 264 patches can be $\Delta E=0.95$. If the scanner is corrected for a lithographic medium, and the test scan is photographic, the error can increase to $\Delta E=4.68$. Examination of pictorial images shows objectionable color-casts resulting from use of incorrect profiles. Even when the correct profile is chosen, there can be sufficient variation in input materials within a given media class to give rise to objectionable errors in scanner color correction.

In order to address these issues, a scanner calibration system is proposed in U.S. application Ser. No. 10/093,220, filed Mar. 6, 2003 by Raja Balasubramanian, Lingappa K. Mestha and Robert J. Rolleston, entitled "Use of Spectral Sensors for Automatic Media Identification and Improved Scanner Correction", which uses a spectrophotometric sensor attached to the scanner. After an image has been scanned, an image processing unit within the scanning application analyzes the image to look for a small set of (for example, 10) locations within the image that satisfy any of the following two criteria: (i) they are smoothly varying regions, and (ii) the colors are sufficiently distinct from each other that they reasonably span the color space. These locations are then used to drive a spectrophotometer sensor that makes spectral measurements at each of these locations. Measurements are then used to refine the color correction for the particular image being scanned. If individual colors/pixels can be calibrated using the spectrophotometer, then the outputs can be device and media independent. Although that system does relate to the use of an in-line spectrophotometer for calibrating the scanners, it is submitted that it would not lead to a general purpose full width array scanning spectrophotometer because it would be too bulky and slow for calibrating individual pixels, and other distinctions.

U.S. Pat. No. 6,031,618, issued Feb. 29, 2000 by Shen-Ge Wang, entitled "Apparatus and Method for Attribute Identification in Color Reproduction Devices" (D/98015) teaches a method of automatic media identification by coating one of the sensors in the linear detector array with an extra color. This signal combined with an estimate of the uncoated sensor output provides 6 signals per channel, which is shown to provide a reliable means of media identification. However, the method does not address the problem in (ii) in the previous paragraph, etc.

U.S. Pat. No. 5,481,380, issued Jan. 2, 1996 by Gunter Bestmann teaches a method of scanner calibration in which a test target containing patches of known calorimetric values is scanned. The resulting scanner RGB values are transformed to estimates of calorimetric values using a simple scanner model, and the estimates are then refined with the known measurements. This approach does not address the issues of scanner calibration without user intervention, etc. According to this Bestmann approach the user should read different test targets for different print samples (for example, a test target #1 for a lithographic print, a test target #2 for a xerographic print, etc.) and construct and store the scanner profile for prints corresponding to those matching samples. However, this will be a tedious and time-consuming process for the user. The user has to spend time to lay down the respective test targets by identifying the printing technology of their document, and then build a correction profile. The targets have to be read by an expensive spectrophotometer. Hence Bestmann's approach is not very attractive for building scanner profiles automatically, although it may have the ability to give end results similar to a scanning spectrophotometer as disclosed herein.

The present inventors have documented a color image sensor chip with multiple photo-sites (as used in an imaging array or bar) as described in the above cited Xerox Corp. U.S. Pat. No. 6,621,576 B2, issued Sep. 16, 2003 to Jagdish C. Tandon and Lingappa K. Mestha, entitled "Color Imager Bar Based Spectrophotometer For Color Printer Color Control System". Also, U.S. Pat. No. 6,556,300, issued Apr. 29, 2003 to Jagdish C. Tandon, et al, entitled "Color Imager Bar Based Spectrophotometer Photodetector Optical Orientation" and U.S. Pat. No. 6,567,170, issued May 20, 2003 to Jagdish C. Tandon, et al, entitled "Simultaneous Plural Colors Analysis Spectrophotometer" are noted, along with other patents cited above, as a detector and data acquisition assembly for a faster and lower cost spectrophotometer implementation. The full width array spectrophotometer embodiment disclosed herein may use a full width array photodetector assembly imaging bar made from bonded plural multiple such color image bar chips having light detectors and color filters as described, for example, in said above U.S. Pat. No. 6,621,576 B2. However, as will be noted, the illumination system disclosed herein is not the same.

The low cost and compact spectrophotometer of various of the above cited Xerox Corp patents can measure the color quality of printed documents and other items, as described therein. (That can include the gray balancing of color printer engines.) For example, by making measurements of color patches on printed test sheets over a small imaged area of 2.4 mm×5.6 mm (calculated for a paper speed of approximately 795 mm/sec) on a minimum moving patch size of 18.4 mm×18.4 mm. Typically approximately 4 milliseconds is currently needed for a test patch read, and during this read, with an approximately 795 mm/sec paper speed, that color test patch will move approximately 3.2 mm.

However, there is a need to make spectral measurements over an entire document, in real time, in some cases. In order to address the problems and issues mentioned above, disclosed herein is a low cost scanning spectrophotometer based on full document width color imaging (image sensor) bars such as those used in Xerox and other document scanners. As noted in the above-cited U.S. Pat. No. 6,621,576 B2, such commercial mass-produced low cost document imaging bars are constructed from multiple individual chips, each having multiple very small and closely spaced photo-sites. Each such chip may be about 16 mm long. Typically each such chip has three rows of such photo-sites manufactured with respective integral color filters for red, green and blue. The spectrophotometer described in said U.S. Pat. No. 6,621,576 B2 uses such chips as photodetectors. Each said chip can read at a resolution of 400 SPI in the x-direction and 600 SPI in the y-direction, and provides 248 photosensitive cells, with a 63.5 micro-meter pitch between cells. The cells contain in-built integration hardware to accumulate photo-generated electrons and amplify the signals. A fourth row of such photo-sites or photocells may be added to these chips, for white light or other sensing. Data is collected from these image bar cells (photo-sites), whenever a target lighting source is sequentially illuminated. The photocells outputs are then processed using spectral reconstruction algorithms, such as those described in patents or applications cited herein, or therein, to produce reflectance spectral signals. The measured pixels can thus be in device independent quantity, and hence can be used across various media, inks or toner.

Thus, the description herein need only describe the unique details of the present system, including the unique illumination optics and scanner architecture providing a full width array scanning spectrophotometer.

A specific feature of the specific embodiment disclosed herein is to provide a full width array spectrophotometer for full width scanning color analysis of a printed print media sheet, comprising at least one substantially linear elongated illumination array of closely spaced multiple LED illumination sources of plural different color emissions in a multiply repeated pattern of at least four different colors extending sufficiently in said substantially linear dimension to transversely substantially span a printer paper path to sequentially illuminate with said plural color emissions a transverse illuminated band extending transversely across a printed print media sheet moving in said paper path, and a full width array light imaging bar comprising an elongated array of multiple closely spaced plural colors photodetectors adjacent to and extending substantially parallel to said at least one substantially linear array of closely spaced multiple LED illumination sources of plural different color emissions, said light imaging bar being positioned to receive light reflected from said transverse illuminated band extending transversely across said print media sheet moving in said paper path.

Further specific features disclosed in the embodiment herein, individually or in combination, include those wherein two substantially linear arrays of closely spaced multiple LED illumination sources of plural different color emissions extending sufficiently in said substantially linear dimension to transversely substantially span a printer paper path to sequentially illuminate with plural colors said transverse illuminated band extending transversely across said print media sheet moving in said paper path, said two said substantially linear arrays of closely spaced multiple LED illumination sources of plural different color emissions being mounted on opposite sides of said full width array light imaging bar and both oriented to illuminate said same transverse illuminated band extending transversely across said sheet of print media moving in said paper path; and/or wherein a SELFOC lens is positioned between said full width array imaging bar and said transverse illuminated band extending transversely across said sheet of print media moving in said paper path; and/or wherein a SELFOC lens is operatively positioned between said full width array light imaging bar and said transverse illuminated band extending transversely across said sheet of print media moving in said paper path; and/or wherein said full width array light imaging bar has 3 or 4 rows of differently color filtered said multiple closely spaced photodetectors; and/or wherein said substantially linear elongated array of closely spaced multiple LED illumination sources of plural different color emissions is in a multiply repeated pattern of at least four different colors extending sufficiently in said substantially linear dimension to transversely substantially span a printer paper path to sequentially illuminate with said plural color emissions said transverse illuminated band transversely across a printed print media sheet moving in said paper path is sequentially illuminated in said multiply repeated pattern of at least four different colors extending along said substantially linear elongated array of closely spaced multiple LED illumination sources; and/or a full width array spectrophotometer for full width scanning color analysis of transversely extensive color test targets in a test target path, comprising at least one substantially linear elongated array of multiple illumination sources of plural different color emissions from multiple different LEDs in a multiply repeated pattern of at least three different colors, said substantially linear elongated array of illumination sources transversely spanning said test target path and sequentially illuminating, in said repeated patterns of at least 3 different color LEDs, a transverse illumination band of said test target path, and an elongated light imaging bar mounted parallel to said at least one substantially linear elongated array of multiple illumination sources, said light imaging bar comprising an elongated array of multiple closely spaced different color sensitive photodetectors, which light imaging bar is positioned to detect and analyze light reflected from said transverse illumination band; and/or wherein said transversely extensive color test targets in a test target path are color printed sheets moving in a xerographic color printer path; and/or a method of full width scanning color analysis of transversely extensive color test targets in a test target path with a full width array spectrophotometer, comprising sequentially illuminating at least one substantially linear elongated array of closely spaced multiple LED illumination sources of plural different color emissions in a multiply repeated pattern of at least three different color LEDs, said substantially linear elongated array of closely spaced multiple illumination sources transversely spanning said test target path to sequentially illuminate, in said repeated patterns of at least three different color LEDs, a transverse illuminated band of said color test targets in said test target path, and detecting and analyzing light reflected from said sequentially illuminated transverse illumination band with an elongated light imaging bar mounted parallel to said at least one substantially linear elongated array of multiple illumination sources, said light imaging bar comprising a parallel and correspondingly elongated array of multiple closely spaced different color sensitive photodetectors; and/or a method of full transverse scanning color analysis of color printed sheets moving in a color printer path with a full width array spectrophotometer, comprising sequentially illuminating at least one substantially linear elongated array of closely spaced multiple LED illumination sources of plural different color emissions in a multiply repeated pattern of different colors extending sufficiently in said substantially linear dimension to transversely substantially span said color printer path to sequentially illuminate with said plural color emissions a transverse illuminated band extending transversely across said color printed sheets moving in said color printer path, and detecting reflected light from said sequentially illuminated band with a full width array light imaging bar comprising an elongated array of multiple closely spaced plural colors photodetectors adjacent to and extending substantially parallel to said at least one substantially linear array of closely spaced multiple LED illumination sources of plural different color emissions, said light imaging bar being positioned to receive light reflected from said transverse illuminated band fully across said print media sheet moving in said paper path.

The disclosed system may be operated and controlled by appropriate operation of conventional control systems. It is well known and preferable to program and execute such control functions and logic with software instructions for conventional or general purpose microprocessors, as taught by numerous prior patents and commercial products. Such programming or software may of course vary depending on the particular functions, software type, and microprocessor or other computer system utilized, but will be available to, or readily programmable without undue experimentation from, functional descriptions, such as those provided herein, in the cited prior patents and applications herein, and/or prior knowledge of functions which are conventional, together with general knowledge in the software or computer arts. Alternatively, the disclosed control systems or methods may be implemented partially or fully in hardware, using standard logic circuits or single chip VLSI designs.

The term "reproduction apparatus" or "printer" as used herein broadly encompasses various printers, copiers or multifunction machines or systems, xerographic or otherwise. The term "sheet" herein refers to a usually flimsy physical sheet of paper, plastic, or other suitable physical substrate for images, whether precut or web fed.

As to specific components of the subject apparatus or methods, or alternatives therefor, it will be appreciated that, as is normally the case, some such components are known per se in other apparatus or applications, which may be additionally or alternatively used herein, including those from art cited herein. For example, it will be appreciated by respective engineers and others that many of the particular components and component actuations or drive systems noted herein are merely exemplary, and that the same novel functions can be provided by many other known or readily available alternatives. All cited references, and their references, are incorporated by reference herein where appropriate for teachings of additional or alternative details, features, and/or technical background. What is well known to those skilled in the art need not be described herein.

Various of the above-mentioned and further features and advantages will be apparent to those skilled in the art from the specific apparatus and its operation or methods described in the example below, and the claims. Thus, the present invention will be better understood from this description of this specific embodiment, including the drawing figures (which are approximately to scale) wherein:

Figure 1:
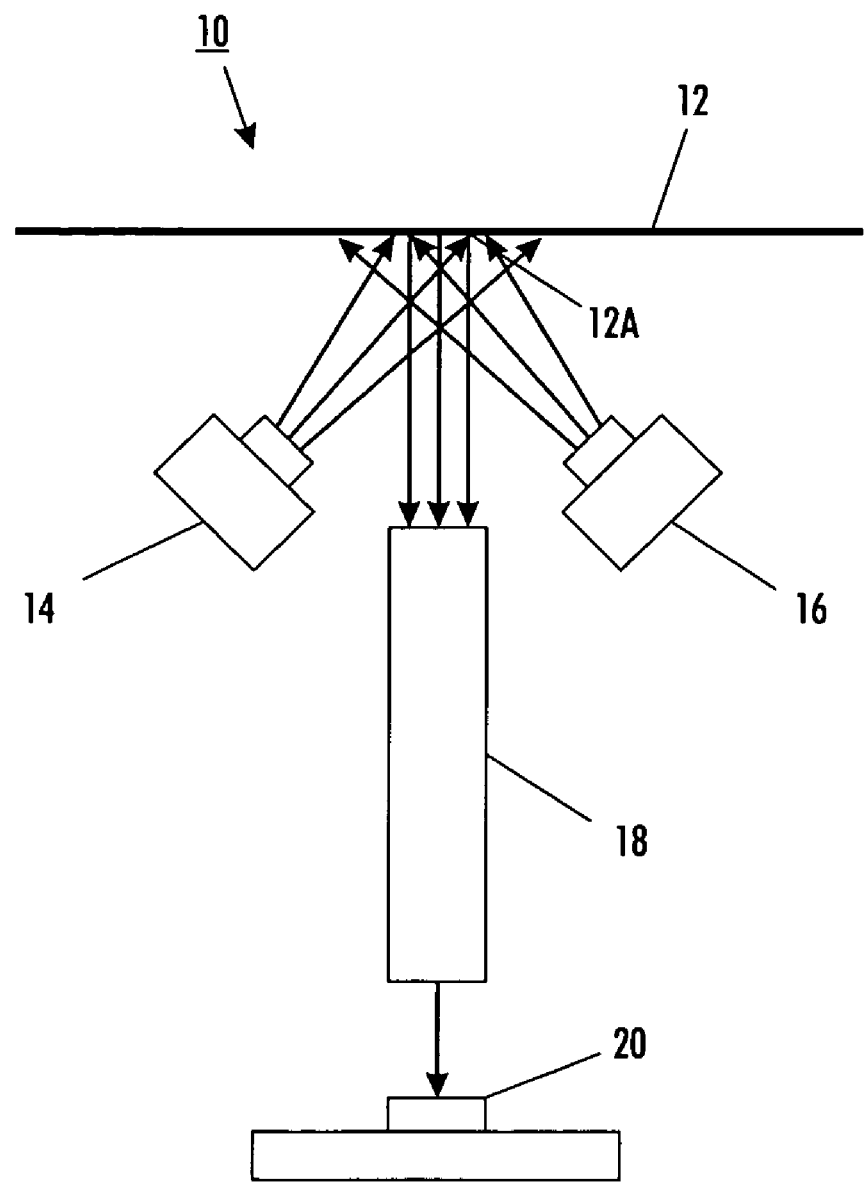
FIG. 1 is a schematic side view of one example of the subject full width scanning spectrophotometer, shown scanning a printed sheet in the output path of a xerographic printer.

Describing now in further detail the exemplary embodiment with reference to the Figures, they illustrate one example of the subject concept for a full width array scanning spectrophotometer system 10. The document 12 to be scanned is illuminated in an illumination strip 12A by a two-sided LED illuminator 14, 16, as will be further discussed below. A SELFOC lens 18 may be used to perpendicularly image the central area of the illuminated strip 12A onto a 3 or 4 row full width array (FWA) image sensor 20. The entire spectrophotometer image module 10 consisting of the illuminator 14, 16, the lens 18 and the FWA image sensor 20 may be stationery, with the document moved over it using a constant velocity transport, such as in a normal paper output path of an otherwise conventional color printer, as in FIG. 1 (see further examples in references cited above), or otherwise. Alternatively, the document could be stationary and the image module could be moved at a constant velocity, as is done in many platen document scanners.

As additionally discussed in the above references such as U.S. Pat. No. 6,690,471 B2, by sequentially activating four different color output LEDs in the LED illuminators 14, 16, eight or twelve different spectral measurements can be made using 3 or 4 row image sensor arrays 20. These measurements can then be converted into the appropriate spectral or L*a*b* values using the algorithms of the above cited references thereon, or others. This scanning spectrophotometer 10 can thus provide higher quality color information compared to a simple RGB scanner due to said 8 to 12 measurements as opposed to only 3 measurements. However, this FWA spectrometer 10 can also be much faster than said prior spectrophotometers that provide only a single area, single test patch, reading point at a time measurement.

Figure 2:
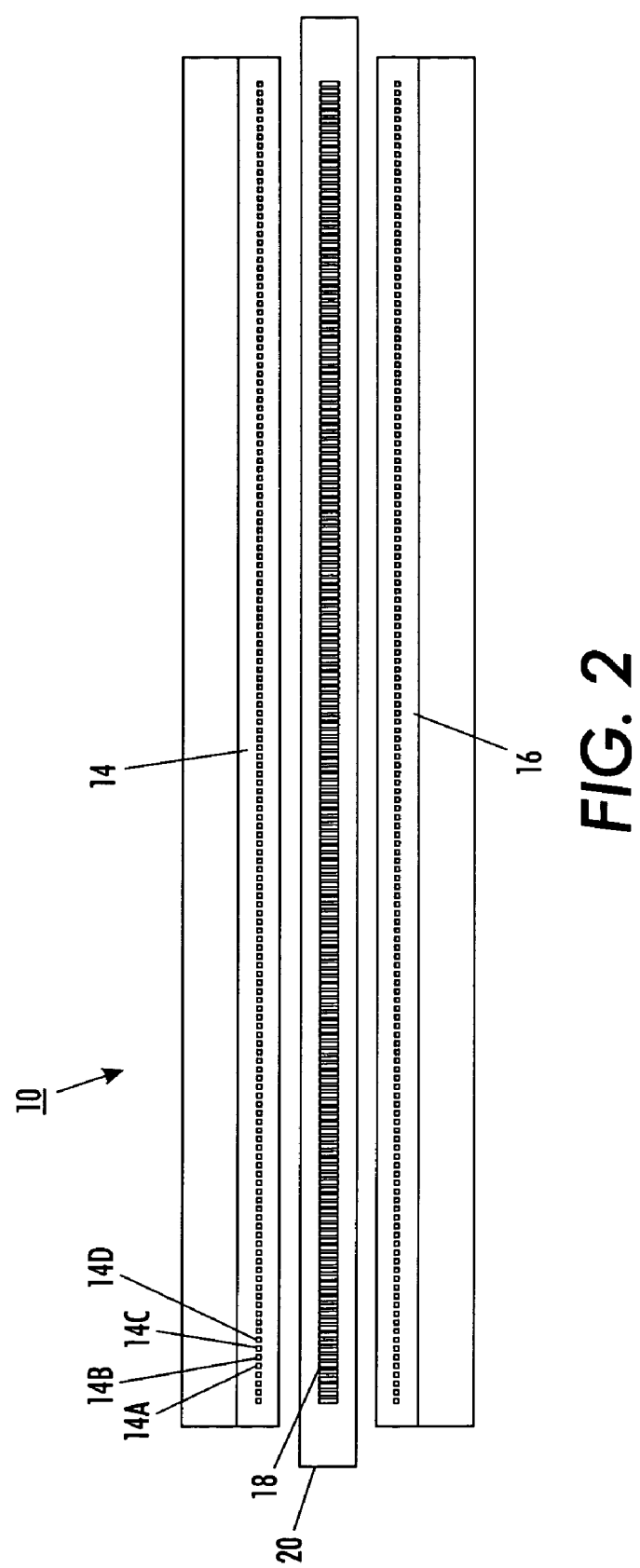
FIG. 2 is a top view thereof, without any printed sheet or other color test object present.

The illuminator here consists of two linear LED arrays 14, 16, one on each side of the SELFOC lens 18 and imaging bar 20, as shown. (A single linear LED array may also be possible as an alternative.) Three or four different types of LEDs may be used in the LED array. In the view of FIG. 2, in illuminator linear array 14, the sequential pattern of 4 individual adjacent LEDs 14A, 14B, 14C, 14D, is shown enlarged for illustrative clarity. LEDs 14A, 14B, 14C, 14D, could be, for example, white, 430 nm, 505 nm and 595 nm LEDs, respectively. All LEDs of one kind (for example, all 14A LEDs) may desirably be turned on together and their resultant transversely adjacent image sensor array 20 multiple output signals captured substantially simultaneously. This process may be rapidly repeated as a fast scan with the next set of white, 430 nm, 505 nm and 595 nm LEDs being illuminated next to illuminate the next lateral portion of test strip 12A and being detected by the next corresponding set of 4 rows of 3 or 4 differently color filtered photodetectors along the imager array 20, and so on. As previously explained above, at least one of the 4 LED illumination colors in this linear illumination array can be white, from white LEDs, or alternatively only three different color LEDs can be used. A full width array of illuminations can alternately be provided by the use of intermediate shaped plastic light guides splitting or spreading the light from a light source at one edge of the full width illuminator, such as is disclosed in Canon U.S. Pat. No. 6,473,154 for a document scanner. As explained above, with a set of 4 different color LEDs selected at a time, illuminating a 4 row (4 colors) image sensor 20, 12 different color measurements are available at a time (8 measurements with a 3 row image sensor).

FIG. 1 shows both LED arrays 14, 16 of the illumination system (which may be commonly mounted on a single printed circuit board) oppositely oriented at about 45 degrees to the test strip 12A they are both illuminating. Thus they allow perpendicular orientation, in between LED arrays 14 and 16, of a linear reflected light optical path from 12A to the imager array 20 through SELFOC lens 18. However, this is not necessarily the most efficient or optimum arrangement for the LEDs. One could alternatively use light guides or lens arrangements to transfer light from LEDs to the document 12. Examples and details of these can be found in some of the above references. Also, instead of using 2 LED arrays 14 and 16 as shown, one could use an LED array on one side and a reflective mirror on the other side, as is typically done with current document scanners using fluorescent illuminators.

Design speed and resolution of the FWA scanning spectrophotometer 10 and it's components would empirically determine the maximum "on" times available for each of the four sets of LEDs and also the maximum integration times available for the different rows of photosites on the image sensor array 20. Both the LED "on" times and the photosite row integration times can be adjusted to provide an adequate signal for each of the 8 to 12 measurements. The x or transverse direction resolution of the scanning spectrophotometer 10 is controlled by the selected image sensor 20 resolution, which is typically 400 to 600 samples or pixels per inch. The Y or process direction resolution would depend on the document 12 velocity as well as the number of different types of LEDs used.

Just as in regular document image scanners, the scanning spectrophotometer 10 may use pixel level gain and offset calibration. Gain calibration compensates for the spatial variations of the LED illuminators as well as image sensor 20 variations. This would be done with each type of LED. The offset calibration compensates for the image sensor array and the electronics variations across the entire array. If considerably different integration times are used with different types of LEDs, offset calibration would desirably be repeated for each different type of LED.

Examples of five spectral reconstruction algorithms are shown in the above-cited U.S. Patents Nos. U.S. Pat. No. 5,963,244, et al. Also noted are the cited 6,690,471 B2 and 6,621,576 B2. The spectral values may then be converted to trichromatic numbers (L*a*b* or XYZ, etc.) for each pixel. The complexity of such an algorithm is typically measured by its computational speed. Study has shown that a DLS algorithm, as described in the above-cited U.S. application Ser. No. 10/758,096, can provide high accuracy provided a good reference database can be constructed. The DLS algorithm can be used with a cellularized database for improving the speed. Algorithms may be implemented in an embedded microprocessor. With an 800 MHz microprocessor each spectral reconstruction would take about 30 ms. Thus, further speed optimization is possible, which is likely to give good spectral accuracy with reduced speed.

The reference database may be constructed and customized for each of the scanning spectrophotometers using similar techniques to that of present spectrophotometers. While constructing the reference database an accurate reference spectrophotometer may be used to characterize the proposed LED scanning spectrophotometer.

As will be appreciated by color technologists, these FWA scanning spectrophotometers spectral measurements can be used for better diagnostics and control of colors from one or more color print engines. Examples include: 1) output engine page non-uniformity measurements and their correction; 2) spatial gray balance with fine quantization for half tone array (smoother tone degradation, improved resolution in tone development, contour free calibration), as described in Xerox Corp. U.S. application Ser. No. 10/342,873, filed Jan. 15, 2003 by Van de Capelle, et al, entitled "Iterative Printer Control and Color Balancing System and Method Using a High Quantization Resolution Halftone Array to Achieve Improved Image Quality with Reduced Processing Overhead," projected publication date of Jul. 15, 2004; 3) remote diagnostics; 4) remote soft proofing of device and media independent images.

In addition to the above-mentioned applications, some other current problems can be addressed. As previously mentioned, users can make mistakes in selecting correct profiles for processing a given scan by examining prints from photographic, offset, and inkjet printers. Considerable errors can be created in choosing an incorrect scanner profile. In contrast, the subject FWA scanning spectrophotometer can be designed to include one profile for all print media, ink, etc. Even when the correct profile is chosen, there can be sufficient variation in input materials within a given media class to give rise to objectionable errors in color correction. As an example of the latter, if the medium is known to be photographic, the scanner's response can change considerably depending on the source of the print medium (for example, Kodak vs. Fuji), and sometimes can vary from batch to batch within the same source. A tedious and time-consuming process of creating different test targets for different print samples (i.e. test target #1 for lithographic print, test target #2 for xerographic print, etc.) and then building correction profiles can be avoided, thus saving productivity for the customer.

Figure 3:
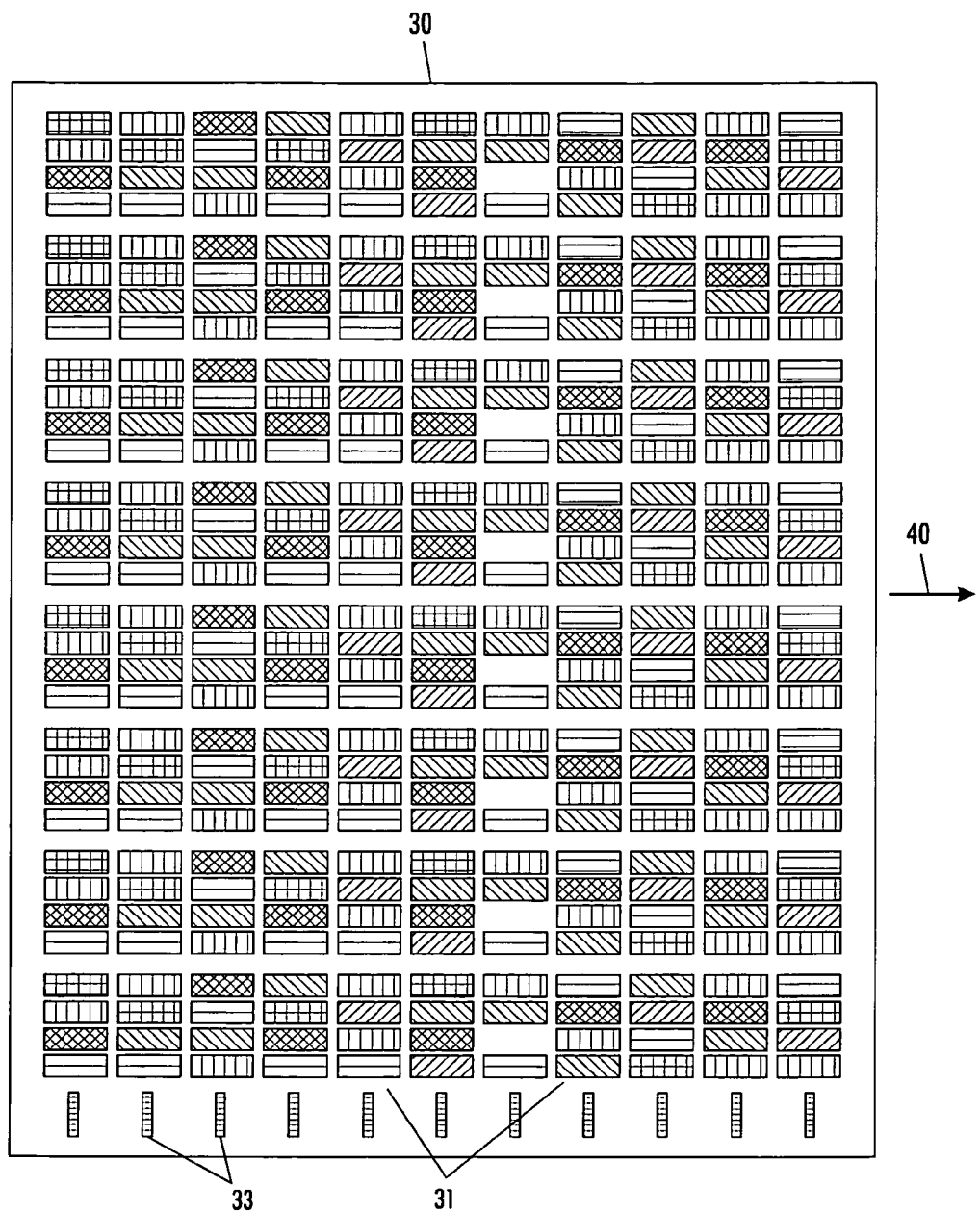
FIG. 3 is one example of a printed test sheet with multiple different colors of test patches that could be used with the full width scanning spectrophotometer of FIGS. 1 and 2.

FIG. 3 is merely one example of a color printer printed test target 30 sheet 12 with rows of different color test patches 31 and timing or triggering indicia marks 33. As described, and shown in FIG. 1, this sheet 12 printed as a full width test target 30 may be moved in the direction of arrow 40 relative to the FWA spectrophotometer 10, or vice versa. As compared to the test sheets shown in the above-cited patents, it may be seen that far more color tests may be performed with the same test sheet, and therefore far less test sheets need be used. That can also reduce printing interruptions for color recalibrations, for different print jobs or different print media, or machine parameter drifts during operations. However, the present system is not limited to use with such test sheets.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A full width array spectrophotometer for full width scanning color analysis of a printed print media sheet, comprising at least one substantially linear elongated illumination array of closely spaced multiple LED illumination sources of plural different color emissions in a multiply repeated pattern of at least four different colors extending sufficiently in said substantially linear dimension to transversely substantially span a printer paper path to sequentially illuminate with said plural color emissions a transverse illuminated band extending transversely across a printed print media sheet moving in said paper path, and a full width array light imaging bar comprising an elongated array of multiple closely spaced plural colors photodetectors adjacent to and extending substantially parallel to said at least one substantially linear array of closely spaced multiple LED illumination sources of plural different color emissions, said light imaging bar being positioned to receive light reflected from said transverse illuminated band extending transversely across said print media sheet moving in said paper path.

2. The full width array spectrophotometer for full width scanning color analysis of a printed print media sheet of claim 1, comprising two substantially linear arrays of closely spaced multiple LED illumination sources of plural different color emissions extending sufficiently in said substantially linear dimension to transversely substantially span a printer paper path to sequentially illuminate with plural colors said transverse illuminated band extending transversely across said print media sheet moving in said paper path, said two said substantially linear arrays of closely spaced multiple LED illumination sources of plural different color emissions being mounted on opposite sides of said full width array light imaging bar and both oriented to illuminate said same transverse illuminated band extending transversely across said sheet of print media moving in said paper path.

3. The full width array spectrophotometer for full width scanning color analysis of a printed print media sheet of claim 1, wherein a SELFOC lens is positioned between said full width array imaging bar and said transverse illuminated band extending transversely across said sheet of print media moving in said paper path.

4. The full width array spectrophotometer for full width scanning color analysis of a printed print media sheet of claim 2, wherein a SELFOC lens is operatively positioned between said full width array light imaging bar and said transverse illuminated band extending transversely across said sheet of print media moving in said paper path.

5. The full width array spectrophotometer for full width scanning color analysis of a printed print media sheet of claim 1, wherein said full width array light imaging bar has three or four rows of differently color filtered said multiple closely spaced photodetectors.

6. The full width array spectrophotometer for full width scanning color analysis of a printed print media sheet of claim 1, wherein said substantially linear elongated array of closely spaced multiple LED illumination sources of plural different color emissions is in a multiply repeated pattern of at least four different colors extending sufficiently in said substantially linear dimension to transversely substantially span a printer paper path to sequentially illuminate with said plural color emissions said transverse illuminated band transversely across a printed print media sheet moving in said paper path is sequentially illuminated in said multiply repeated pattern of at least four different colors extending along said substantially linear elongated array of closely spaced multiple LED illumination sources.

7. A full width array spectrophotometer for full width scanning color analysis of transversely extensive color test targets in a test target path, comprising:

at least one substantially linear elongated array of multiple illumination sources of plural different color emissions from multiple different LEDs in a multiply repeated pattern of at least three different colors, said substantially linear elongated array of illumination sources transversely spanning said test target path and sequentially illuminating, in said repeated patterns of at least three different color LEDs, a transverse illumination band of said test target path, and an elongated light imaging bar mounted parallel to said at least one substantially linear elongated array of multiple illumination sources, said light imaging bar comprising an elongated array of multiple closely spaced different color sensitive photodetectors, which light imaging bar is positioned to detect and analyze light reflected from said transverse illumination band.

8. The full width array spectrophotometer of claim 7, wherein said transversely extensive color test targets in a test target path are color printed sheets moving in a xerographic color printer path.

9. A method of full width scanning color analysis of transversely extensive color test targets in a test target path with a full width array spectrophotometer, comprising:

sequentially illuminating at least one substantially linear elongated array of closely spaced multiple LED illumination sources of plural different color emissions in a multiply repeated pattern of at least three different color LEDs, said substantially linear elongated array of closely spaced multiple illumination sources transversely spanning said test target path to sequentially illuminate, in said repeated patterns of at least three different color LEDs, a transverse illuminated band of said color test targets in said test target path, and detecting and analyzing light reflected from said sequentially illuminated transverse illumination band with an elongated light imaging bar mounted parallel to said at least one substantially linear elongated array of multiple illumination sources, said light imaging bar comprising a parallel and correspondingly elongated array of multiple closely spaced different color sensitive photodetectors.

10. A method of full transverse scanning color analysis of color printed sheets moving in a color printer path with a full width array spectrophotometer, comprising:

sequentially illuminating at least one substantially linear elongated array of closely spaced multiple LED illumination sources of plural different color emissions in a multiply repeated pattern of different colors extending sufficiently in said substantially linear dimension to transversely substantially span said color printer path to sequentially illuminate with said plural color emissions a transverse illuminated band extending transversely across said color printed sheets moving in said color printer path, and detecting reflected light from said sequentially illuminated band with a full width array light imaging bar comprising an elongated array of multiple closely spaced plural colors photodetectors adjacent to and extending substantially parallel to said at least one substantially linear array of closely spaced multiple LED illumination sources of plural different color emissions, said light imaging bar being positioned to receive light reflected from said transverse illuminated band fully across said print media sheet moving in said paper path.

\* \* \* \* \*